(12) United States Patent
Gagné et al.

(10) Patent No.: US 8,594,417 B2
(45) Date of Patent: Nov. 26, 2013

(54) SYSTEMS AND METHODS FOR INSPECTING ANODES AND SMELTING MANAGEMENT RELATING TO THE SAME

(75) Inventors: Jean-Pierre Gagné, Chicoutimi (CA); Gilles Dufour, Quebec (CA)

(73) Assignee: ALCOA Inc., Pittsburgh, PA (US)

( * ) Notice: Subject to any disclaimer, the term of this patent is extended or adjusted under 35 U.S.C. 154(b) by 1087 days.

(21) Appl. No.: 11/946,000

(22) Filed: Nov. 27, 2007

(65) Prior Publication Data

US 2009/0136122 A1 May 28, 2009

(51) Int. Cl.
*G06K 9/00* (2006.01)

(52) U.S. Cl.
USPC ............. 382/152; 382/106; 382/143; 205/91; 205/80

(58) Field of Classification Search
USPC .......... 382/152, 217, 619; 209/625, 602, 601; 205/80, 81, 82, 96; 356/237.1–237.6, 356/601, 614; 250/311, 559.07, 559.08, 250/559.19, 559.22, 559.23, 559.34, 374, 250/38, 5.1, 225; 204/192.32, 192.34, 204/192.38, 298.41
See application file for complete search history.

(56) References Cited

U.S. PATENT DOCUMENTS

| | | | | |
|---|---|---|---|---|
| 4,399,008 A * | 8/1983 | Ray | ................ | 205/387 |
| 4,399,088 A * | 8/1983 | Greene | ................ | 264/54 |
| 4,921,584 A * | 5/1990 | Koski et al. | ................ | 205/336 |
| 5,268,083 A * | 12/1993 | Rathgeber et al. | ............. | 72/302 |
| 6,251,238 B1 * | 6/2001 | Kaufman et al. | ............. | 204/242 |
| 6,870,953 B2 * | 3/2005 | Suzuki et al. | ................ | 382/152 |
| 7,001,497 B2 * | 2/2006 | Gagne et al. | ................ | 205/81 |
| 7,728,797 B2 * | 6/2010 | Nagayama | ................ | 345/76 |
| 2002/0038510 A1 * | 4/2002 | Savareigo et al. | ............. | 29/846 |
| 2003/0150715 A1 * | 8/2003 | Yahalom et al. | ........... | 204/229.1 |
| 2007/0125660 A1 * | 6/2007 | Barclay et al. | ............... | 205/376 |
| 2007/0214626 A1 * | 9/2007 | Fidjeland | .................. | 29/402.01 |
| 2008/0097135 A1 * | 4/2008 | Dumont et al. | ............... | 588/249 |
| 2008/0307625 A1 * | 12/2008 | Lescarcelle | ............... | 29/402.08 |
| 2009/0066933 A1 | 3/2009 | Takano et al. | .................. | 356/32 |

FOREIGN PATENT DOCUMENTS

| | | | |
|---|---|---|---|
| CA | 2390536 | 5/2001 | |
| EP | 0597639 | 5/1994 | |
| EP | 1128179 | 8/2001 | |
| JP | 63281007 A * | 11/1988 | ............. G01B 11/24 |

(Continued)

OTHER PUBLICATIONS

Gagne et al. "Anode stubs inspection system", Light Metals 2007, 2007, p. 1021-4, 0 refs, Publisher: Minerals, Metals & Materials Society, Warrendale, PA, USA.Light Metals 2007, Orlando, FL, USA, Feb. 25-Mar. 1, 2007.*

(Continued)

*Primary Examiner* — Mekonen Bekele
(74) *Attorney, Agent, or Firm* — Greenberg Traurig, LLP

(57) ABSTRACT

Systems and methods for inspecting anodes, and smelting management based thereon are provided. In one embodiment, a system includes an imaging device configured to obtain images of at least one anode assembly, an image processor configured to producing imaging data based on the images, and a data analyzer configured to produce anode characteristic data based on the imaging data. In one embodiment, a method includes the steps of obtaining at least one image of at least a portion of an anode assembly, producing imaging data based on the at least one image, and deriving anode characteristic data based, at least in part, on the imaging data.

8 Claims, 19 Drawing Sheets

(56) References Cited

FOREIGN PATENT DOCUMENTS

| JP | 2006045609 A | * | 2/2006 | ............... C25C 1/00 |
|---|---|---|---|---|
| WO | WO 98/36240 | | 8/1998 | |
| WO | WO 03/035940 | | 5/2003 | |
| WO | WO 2004/018738 | | 3/2004 | |
| WO | WO 2004018738 A1 | * | 3/2004 | ............... C25C 3/12 |
| WO | WO 2006/104110 | | 10/2006 | |

OTHER PUBLICATIONS

Jayson.et al.(hereafter Jayson), "Anode cover material estimation using image analysis in primary aluminium production Automation in Mining, Mineral and Metal Processing", published 12th IFAC Symposium on Automation in Mining, Mineral and Metal Processing, held between Aug. 21-23, 2007, pp. 11.*

Jayson.et al.(hereafter Jayson), "Anode cover material estimation using image analysis in primary aluminium production Automation in Mining, Mineral and Metal Processing", published 12th IFAC Symposium on Automation in Mining, Mineral and Metal Processing, held between Aug. 21-23, 2007, pp. 11.*

Gagne et al., *Anode Butts Automated Visual Inspection System*, The Minerals, Metals & Materials Society, pp. 1-4 (2008).

Gagne et al., *Anode Stubs Inspection System*, The Minerals, Metals & Materials Society, pp. 1-4 (2007).

International Search Report and Written Opinion, dated Feb. 27, 2009, from corresponding International Application No. PCT/US2008/084076.

Office Action, dated Aug. 15, 2013, from related Canadian Application No. 2,744,600.

* cited by examiner

Family 1 – Mushroom/Spike

Family 2 – Belly

Family 3 – Uneven

Family 4 – Heel

Family 5 – Incomplete

Family 6 – Oxidized (top)

Metal Production Data

Potline Data
- Number of cells
- Electrical efficiency
- Downtime
- Maintenance

Electrolysis Cell Data
- Temperature(s)
- Bath ratio(s)
- Bath level
- Alumina feed rate(s)/time(s)
- Electrical efficiency
- Current distribution
- Heat balance
- Metal production rate(s)
- Metal purity
- Tapping frequency
- Anode position within cell
- Anode insertion/removal date(s)/time(s)
- Anode life
- Assigned production crew
- Others (?)

Anode Characteristic Data

·Geometrical features
    -Thickness(es)
    -Defects
        *Mushroom/spike
        *Belly
        *Uneven
        *Heel
        *Incomplete
        *Oxidized
·Lighting differences
    -% of bath on anode
·Pre-use
·Post-use
·Post-recovery

SYSTEMS AND METHODS FOR INSPECTING ANODES AND SMELTING MANAGEMENT RELATING TO THE SAME

BACKGROUND

During the electrolytic production of aluminum, anodes are consumed in the electrolytic process and are thus considered consumables. FIG. 1a illustrates a typical anode assembly prior to use in an electrolytic cell. The anode assembly 40 includes a rod 44 and an unused anode portion 41. FIG. 1b illustrates one embodiment of an anode assembly after use in an electrolytic cell. The assembly anode 40 includes the rod 44 and a used anode portion 42, sometimes referred to herein as an anode butt. Due to processing conditions and placement within the electrolysis cell, the thickness and shape of the anode butt 42 may vary. These variations depend on many factors, such as anode fabrication conditions, raw materials, and electrolysis processing conditions.

SUMMARY OF THE DISCLOSURE

Broadly, the instant disclosure relates to automated or semi-automated anode analysis systems, and methods relating thereto. The systems and methods may be employed to manage smelting activities.

In one aspect, systems relating to anode inspection are provided. In one approach, a system includes an imaging device configured to obtain images of at least one anode assembly, an image processor configured to producing imaging data based on the images, and a data analyzer configured to produce anode characteristic data based on the imaging data. In one embodiment, a system includes a display adapted to display at least some of the anode characteristic data. In one embodiment, the display is remote of the imaging system. In one embodiment, the imaging device and image processor are integral. In one embodiment, the image processor and data analyzer are integral. In one embodiment, the data analyzer is configured to determine geometrical characteristics of an anode assembly based on at least one of the images. In one embodiment, the data analyzer is configured to determine anode thickness. In one embodiment, the data analyzer is configured to determine anode thicknesses for various zones of the anode assembly. In one embodiment, the data analyzer is configured to determine whether the anode is defective.

In another aspect, methods relating to anode inspection and provided. In one approach, a method includes the steps of obtaining at least one image of at least a portion of an anode assembly, producing imaging data based on the at least one image, and deriving anode characteristic data based, at least in part, on the imaging data. In one embodiment, the method includes the step of determining whether an anode assemblies comprises a defect based, at least in part, on the anode characteristic data. In one embodiment, a method includes the step of determining the geometrical characteristics of the anode assembly based, at least in part, on the anode characteristic data. In one embodiment, a method includes the steps of utilizing the anode assembly in an aluminum electrolysis cell, removing the anode assembly from the aluminum electrolysis cell, and determining whether the aluminum electrolysis cell requires adjustment based on the anode characteristic data. In one embodiment, a method includes the steps of producing the anode assembly in an anode producing facility, and determining whether anode production parameters require adjustment based on the anode characteristic data. In one embodiment, a method includes the step of correlating a unique identifier with at least one of the imaging data and the anode characteristic data via a computerized device. In one embodiment, the correlating step includes scanning a member associated with the anode assembly for the unique identifier and communicating, based on the scanning step, the unique identifier to the computerized device. In one embodiment, a method includes utilizing the anode characteristic data to manage smelting activities of an aluminum production facility.

In another aspect, systems relating to smelting management are provided. In one approach, a system includes a conveyor configured to convey anode assemblies through an aluminum smelting facility, an imaging system configured to obtain images of the anode assemblies and produce anode characteristic data based thereon, and a computerized device configured to receive the anode characteristic data. In one embodiment, the system includes a plurality of unique identifiers and a reader configured to read each unique identifier and communicate the unique identifier to at least one of the imaging system and the computerized device. In one embodiment, each unique identifier is associated with an anode assembly, and at least one of the imaging system and the computerized device is configured to correlate each unique identifier to a corresponding anode assembly. In one embodiment, the anode characteristic data includes data relating to each unique identifier correlated to its corresponding anode assembly. In one embodiment, the computerized device is configured to assist in managing smelting facility activities based on the anode characteristic data. In one embodiment, the plurality of unique identifiers includes at least a first set of unique identifiers and a second set of unique identifiers. In one embodiment, the first set of unique identifiers are associated with the anode assemblies, and the second set of unique identifiers are associated with a plurality of electrolysis cells. In one embodiment, the system includes electrolysis cell data obtained from a plurality of electrolysis cells. In one embodiment, the electrolysis cell data includes data relating to each one of the second set of unique identifies correlated to its corresponding electrolysis cell. In this regard, data from each anode assembly may be correlated to data corresponding with the electrolysis cell in which it is used. The correlated data may be used to manage smelting activities. In one embodiment, the computerized device is configured to assist in management of at least some of the plurality of electrolysis cells based, at least in part, on at least some of the electrolysis cell data and at least some of the anode characteristic data.

In yet another aspect, methods relating to smelting management are provided. In one approach, a method includes collecting electrolysis cell data for each of a plurality of aluminum electrolysis cells, collecting anode characteristic data for a plurality of anodes associated with the plurality of aluminum electrolysis cells, correlating the electrolysis cell data and anode characteristic data, and utilizing the anode characteristic data in combination with the electrolysis cell data to manage smelting activities of an aluminum production facility. In one approach, as correlated, the anode characteristic data for each anode assembly corresponds with the electrolysis cell data for the electrolysis cell in which the anode assembly was used.

Various ones of the inventive aspects noted hereinabove may be combined to yield various systems and methods. These and other aspects, advantages, and novel features of the disclosure are set forth in part in the description that follows and will become apparent to those skilled in the art upon examination of the following description and figures, or may be learned by practicing the invention.

BRIEF DESCRIPTION OF THE DRAWINGS

FIG. 11c is a chart illustrating various types of metal production data.

FIG. 11d is a chart illustrating various types of anode characteristic data.

DETAILED DESCRIPTION

Figure 1A:
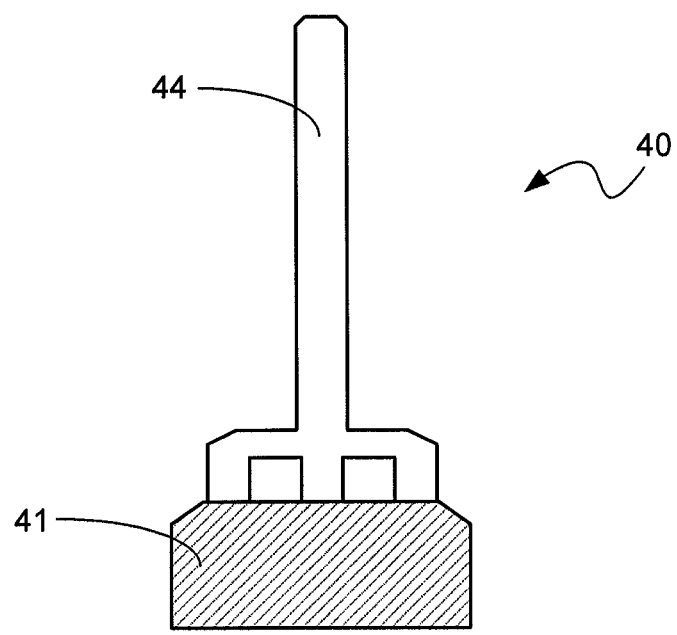
FIG. 1a is a schematic, side view of one embodiment of a conventional, unused anode assembly.
Figure 1B:
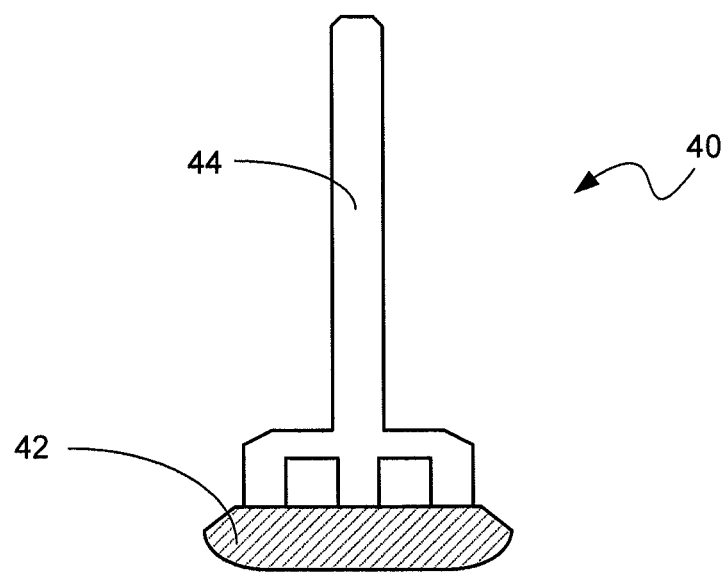
FIG. 1b is a schematic, side view of one embodiment of an anode assembly after use in an electrolytic cell.

Reference is now made to the accompanying figures, which at least assist in illustrating various pertinent features of the instant disclosure.

As noted above, the instant disclosure relates to automated or semi-automated anode analysis systems, and associated methods. The anode analysis systems may be used to facilitate management of smelting activities, such as electrolytic cell operations or anode production. The anode analysis systems may be used to evaluate anodes pre-use (i.e., prior to use in an electrolysis cell), and/or the anode analysis systems may be used to evaluate anodes post-use (i.e., after use in an electrolysis cell). Data collected via the anode analysis systems may be communicated to a controller. The data may be correlated relative to individual anodes or electrolytic cells (e.g., via a data matrix, RFID or transponders, to name a few) to facilitate compilation and analysis of data and analysis of smelting operations. The anode analysis system may be readily integrated with existing smelting facilities and may automatically image and/or measure many, if not all, anodes of a smelting plant.

In one approach, an anode analysis system may obtain images of one or more anode assemblies using artificial vision (e.g., via one or more imaging devices) and produce imaging data based thereon. As used herein, "anode analysis system" means a system including at least one imaging device and at least one image processor for converting images to imaging data. As used herein, "imaging data" means data obtained via analysis of one or more images of an anode assembly, such as pre-use, post-use and/or post-recovery. As used herein, "pre-use" means prior to use in an electrolysis cell. As used herein, "post-use" means after use in an electrolysis cell. As used herein, "post-recovery" means after the anode butt has been removed from the anode rod. Post-recovery is a subset of post-use. The anode analysis system may also obtain physical data relating to one or more anodes. As used herein, "physical data" means data obtained from one or more non-imaging apparatus and relating to an anode assembly. Physical data may be obtained pre-use, post-use, and/or post-recovery. Physical data may include, for example, a weight of the anode assembly or a component thereof. As used herein, "anode characteristic data" means data that includes at least some imaging data, or data derived from imaging data, and may also include some physical data. These anode characteristic data may be communicated to a controller (e.g., a computerized device) and/or displayed to facilitate management of smelting activities. In one embodiment, anode characteristic data are used to manage anode production. For example, and with respect to pre-baked carbon anodes, the anode characteristic data may be used to determine whether carbon paste production parameters (e.g., a coke-to-pitch ratio), green anode formation parameters, or baking parameters, are suitable. In one embodiment, anode characteristic data are used to manage electrolytic cells and/or potlines (a plurality of electrolysis cells connected in series). For example, the anode characteristic data may be used to determine whether one or more electrolysis cells are operating normally, or whether one or more electrolysis cells require adjustment of an operating parameter, maintenance, or other type of management.

Figure 2A:
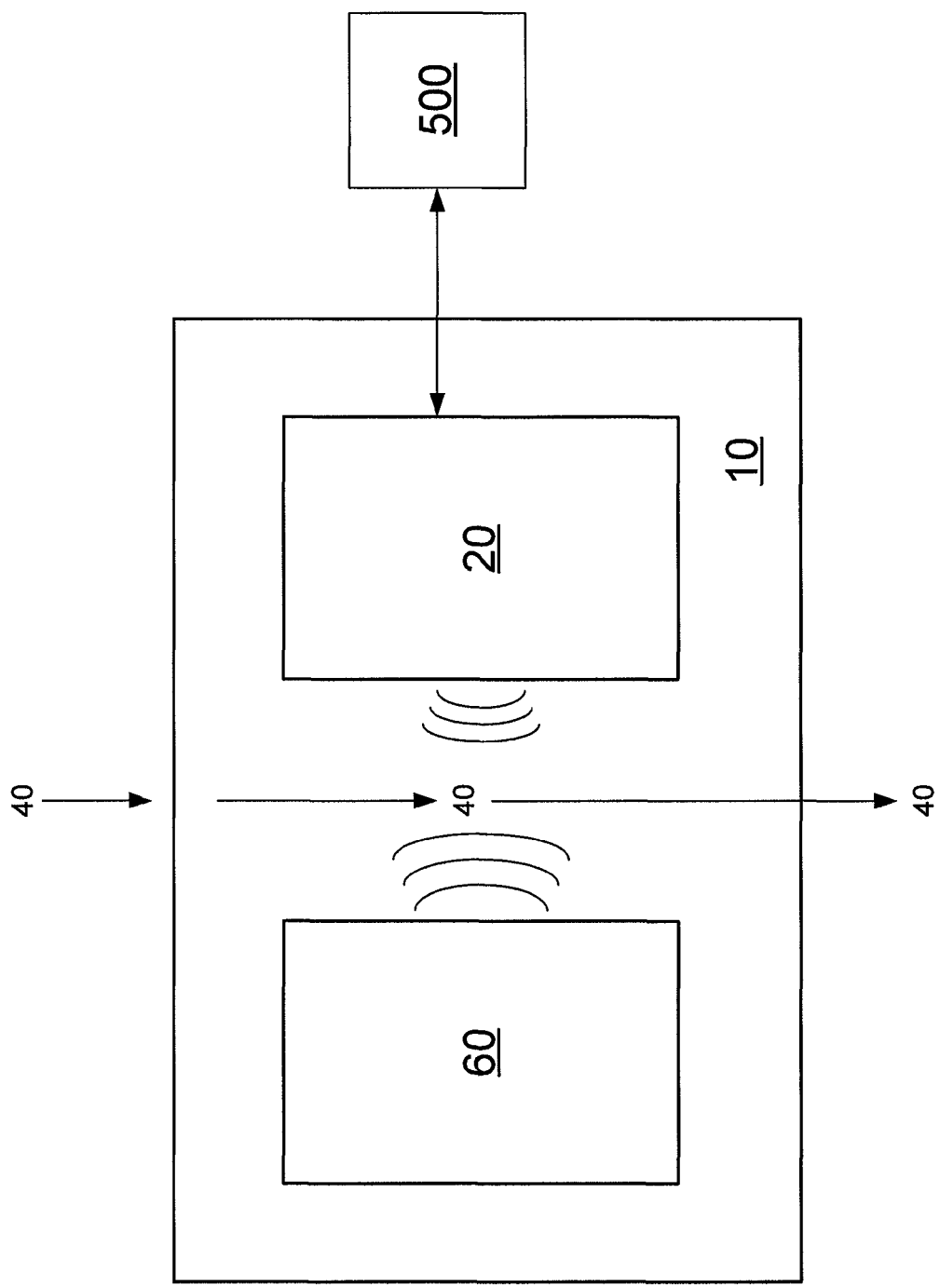
FIG. 2a is a schematic view of one embodiment of an anode analysis system.

One embodiment of an anode analysis system and an imaging methodology is illustrated in FIG. 2a. In the illustrated embodiment, the anode analysis system 10 includes an imaging system 20 adapted to obtain one or more images of at least one anode assembly 40, or a portion thereof. The anode analysis system 10 may include a separate light production apparatus 60 so as to facilitate production of imaging light, such as rear imaging light. Use of consistent imaging light may realize more consistent image production and thus more consistent imaging data. As anode assemblies 40 move to or from a metal production facility, they may pass by the imaging system 20 (e.g., between the imaging system 20 and the light production apparatus 60), at which time the imaging system 20 may capture one or more images of at least some of, or even all of, the anode assemblies. The images may include at least portions of the anode assemblies. As discussed in further detail below, the obtained images may be converted into imaging data, such as via a computerized device. This, and other anode characteristic data, may be communicated, for example, to a control center 500 to facilitate smelting management. In one embodiment, the anode characteristic data and/or graphics and/or text based thereon, are displayed at the computerized device and/or the control center 500. In one embodiment, a proposed course of action is automatically displayed in response to the anode characteristic data. In one embodiment, a controller automatically adjusts a smelting activity in response to the anode characteristic data.

Figure 2B:
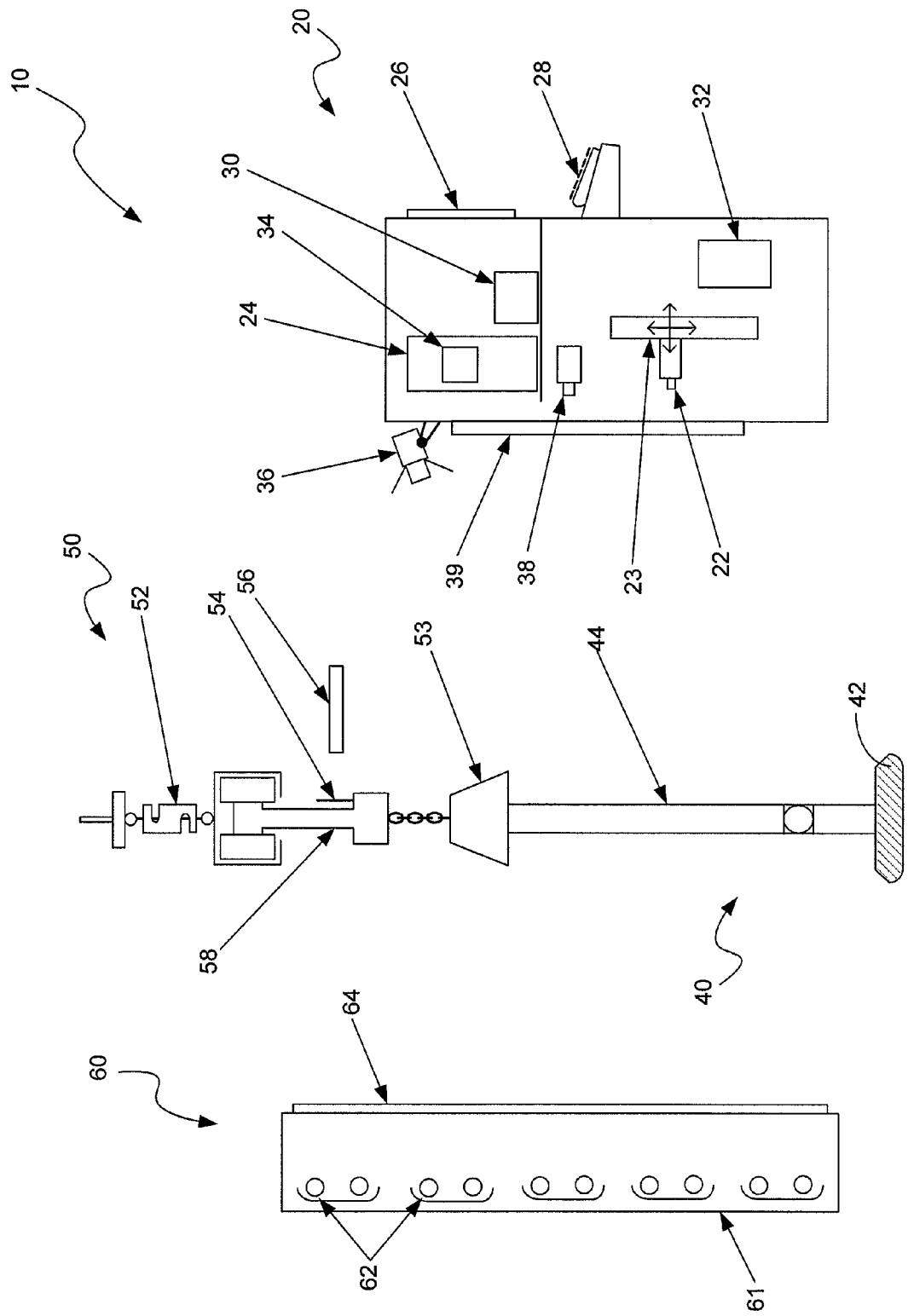
FIG. 2b is a schematic view of one embodiment of an anode analysis system.
Figure 2C:
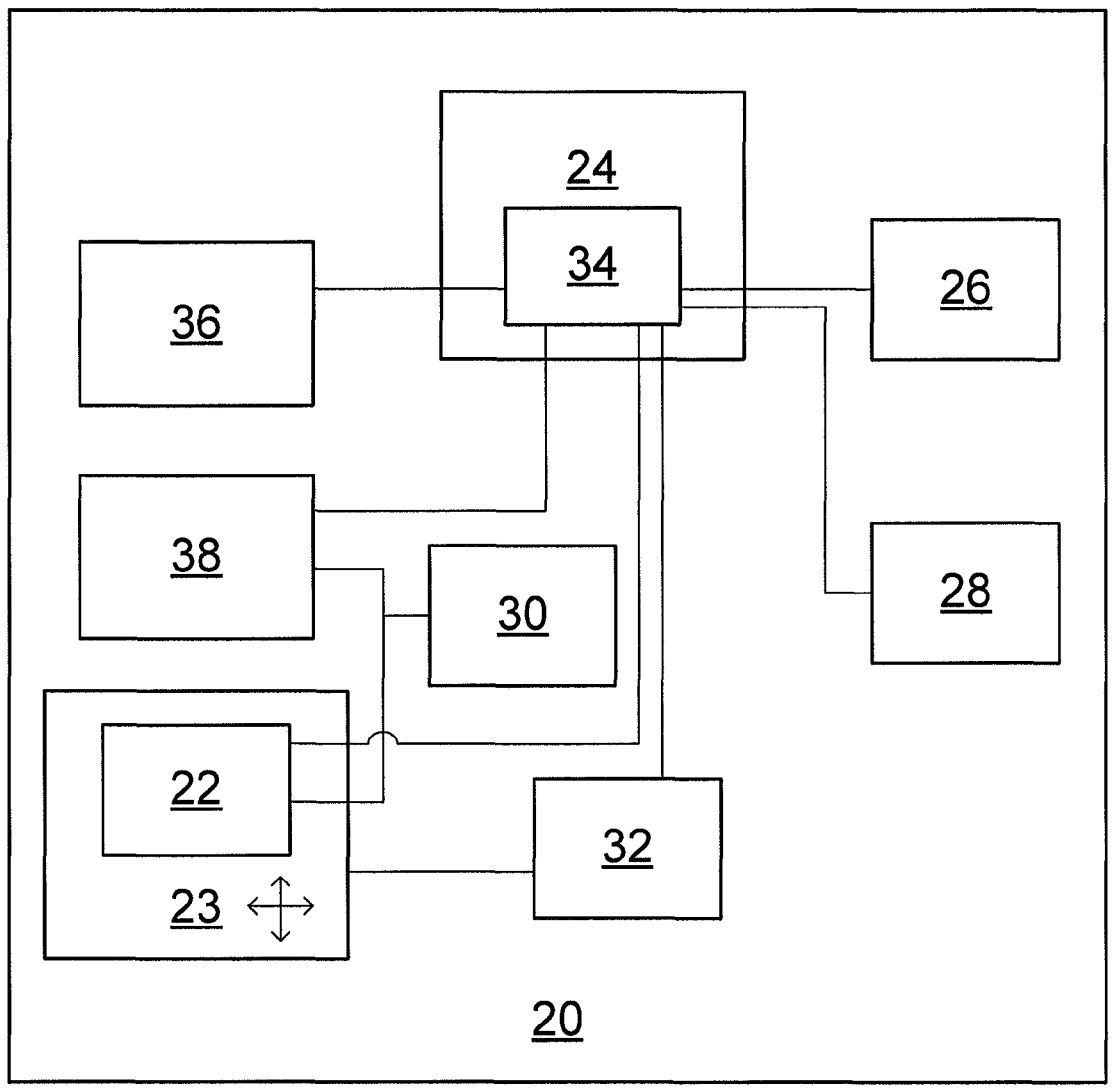
FIG. 2c is a schematic view illustrating electrical and/or physical interconnections of the imaging system of FIG. 2b.

A more particular embodiment of an anode analysis system is illustrated in FIGS. 2b and 2c. In this embodiment, the imaging system 20 includes at least a first imaging device 22 for obtaining images of anodes. As used herein, "imaging device" means any device operable to capture images utilizing electromagnetic radiation, such as a photographic device, a scanner, and an x-ray device, to name a few. The imaging device 22 may operate using digital or analog technology. Digital photographic devices may obtain images in a binary data format that is readily processed by an image processor. Indeed, in one embodiment, the image processor and imaging device 22 may be integrated in a single device. As used herein, "integral", "integrated", and the like, means "to constitute a whole together with other parts or factors." The imaging device 22 may obtain any of several image styles, such as black and white images, color images, infrared images, UV images, x-ray images and combinations thereof, to name a few, to facilitate analysis of anode assemblies 40. In the illustrated embodiment, the first imaging device 22 is operable to obtain images of an anode butt 42 of an anode assembly 40.

The imaging device 22 may be interconnected to a computer 24. The computer 24 may be connected to a display 26 and a keyboard 28, and the computer 24 may include memory, processor and other suitable computer devices/media, as embodied in box 34. The computer 24 may be operable to collect and/or store images and produce imaging data based thereon (e.g., via an image processor). The computer 24 may further be operable to communicate the imaging data to other computerized devices, such as via wired or wireless technology. In one embodiment, a conventional computer utilizing conventional memory, processors, operating software, and image processing software, to name a few of the components, are employed.

As noted above, the imaging device 22 may be any suitable device adapted to obtain images of the anodes. For example, the imaging device 22 may include a digital photographic device. In turn, the image may be in a binary format. In one embodiment, the digital photographic device comprises an image processor. For example, the imaging device may be a digital photographic device including an integrated processor capable of analyzing the image and automatically outputting imaging data based on the obtained image. In turn, the image may be in a binary format.

The imaging system 20 may include a data analyzer (not illustrated) in addition to the imaging device. The data analyzer may be electrically interconnectable to the image processor and may be operable to analyze the imaging data to facilitate approximation of anode assembly properties and/or management of smelting activities. For example an ethernet camera, such those produced by IMPERX or PROSILICON, may be employed as the imaging device, and thus may include an integrated image processor. In turn, an ethernet communications methodology, such as Gigabyte Ethernet, may be used to electrically communicate the imaging data to the data analyzer. In another embodiment, the communications protocol is CAMERA LINK. In one embodiment, the camera is an analog camera (e.g., by JAI AMERICA of Boston, Mass., USA). Other imaging devices and connections may be utilized. The data analyzer may be a part of, for example, computer 24, such as a general purpose computer comprising hardware (e.g., CPU, memory, and so on) and software that enables the computerized device to receive the imaging data and perform calculations based thereon. Upon receipt of the imaging data, the data analyzer may analyze the image characteristic data to facilitate evaluation of the anodes (e.g., approximation of the anode size and/or shape), detection of defects and/or management of smelting activities. In one embodiment, the data analyzer may analyze image characteristic data for a plurality of images to facilitate evaluation of the anodes and/or management of smelting activities.

A lens (not illustrated) may be employed with the imaging device 22. The lens should facilitate capturing of images that provide useful imaging data. Thus, the lens may facilitate capturing of images that provide a macroscopic field of view of the anode assemblies 40. The imaging device 22 is generally positioned proximal the anodes to facilitate obtaining the images and is positioned with the lens of the imaging device 22 directed toward the anode assemblies 40. The distance from a lens to an object, in this case the anode assemblies 40, is generally known as the object distance. The object distance between the imaging device 22 and the anode assemblies 40 is application specific. However, the object distance should be sufficient to obtain a macroscopic image of at least a portion of each anode assemblies 40 and, in some instances, an image of at least the entire anode butt 42 of the anode assemblies 40. In one embodiment, the object distance is at least about 2.5 meters. In a related embodiment, the object distance is not greater than about 5 meters.

The image area produced by an imaging device and lens combination at a specific object distance is generally known as the field of view. The field of view is application specific and is related to the object distance, but the field of view should provide a macroscopic image of the anode assemblies 40. In one embodiment, the obtained images may have a field of view of at least 1.5 meters. In a related embodiment, the field of view may be not greater than 3 meters.

As noted, the first imaging device 22 is operable to obtain images of the anode assembly 40. To facilitate proper placement and image reproduction, the first imaging device 22 may be interconnected to an actuator 23. As used herein, the "actuator" means any device that is operable to move the first imaging device 22 in at least one dimension (e.g., any one of an up, down, and/or side-to-side direction). To facilitate appropriate movement of the first imaging device 22 via the actuator 23, the actuator 23 may be interconnected to servo 32. As used herein, "servo" means any device capable of controlling the actuator 23. The servo 32 may further be interconnected to computer 24 to facilitate movement of the first imaging device 22.

The imaging system 20 may include a lighting unit 36 for directing light toward the anode assembly 40, which may facilitate production of consistent lighting during imaging of the anode assemblies 40. The lighting unit 36 may utilize any suitable wavelength of light to facilitate the production of the images. Use of consistent imaging light may realize more consistent image production and thus more consistent imaging data. In one approach, lighting unit 36 is utilized as a flash. In one embodiment, the lighting unit 36 is utilized to obtain a first image of an anode assembly 40, and the light production apparatus 60 is separately used to obtain a second image of the anode assembly. In one embodiment, light differences between the first and second images may be utilized to determine characteristics of the anode assembly 40 (e.g., an amount of bath residual remaining on the anode assembly).

The imaging system 20 may include one or more additional apparatus to facilitate consistent lighting. For example, the imaging system 20 may include a window 39. The window 39 may be located between the first imaging device 22 and the anode assembly 40. The window 39 may facilitate consistent lighting by allowing only certain wavelengths of light to penetrate the window 39. In one embodiment, the lighting panel window 39 comprises a polymeric or glass material.

The imaging system 20 may include one or more additional imaging devices so as to facilitate imaging of anode assemblies 40 or parts thereof. In the illustrated embodiment, the imaging system 20 includes a second imaging device 38 adapted to obtain images of the anode rods 44. More particularly, the second imaging device 38 is positioned so as to obtain images of a clad portion (not illustrated) of the anode rod 44. Over time, clad portions may become cracked, or include other defects. The second imaging device 38 may obtain images of such clad portions and provide an early indication as to when such clad portions are no longer suitable and/or are defective.

As noted above, one or more imaging devices may be utilized with the imaging system 20. When a plurality of imaging devices are utilized, it may be appropriate to coordinate the activation of the imaging devices so as to facilitate consistent timing of the imaging devices. In this regard, a timer 30 may be utilized to time and/or actuate the plurality of imaging devices. In one embodiment, the timer 30 is integrated with and/or interconnected to the computer 24.

The anode analysis system 10 may include a separate light production apparatus 60 so as to facilitate production of imaging light, such as rear imaging light. Use of consistent imaging light may realize more consistent image production and thus, more consistent imaging data. In the illustrated embodiment, the light production apparatus 60 includes a container 61 comprising a plurality of light producing apparatus, such as light bulbs. The light production apparatus 60 may also include a window 64, such as a window similar to window 39, described above. The light production apparatus 60 may be located on one side of the anode assemblies 40, and the imaging system 20 may be located on another side of the anode assemblies 40. In this regard, the anode assemblies 40 may move between the imaging system 20 and the light production apparatus 60. Thus, the light production apparatus 60 may provide back lighting, which may be contrasted with images obtained with front lighting to determine characteristics of the anode assembly 40.

The anode assemblies 40 may be moved using a conventional conveyor system 50. In the illustrated embodiment, the conveyor system 50 includes a plurality of bells 53, each of which is adapted to interconnect with an anode assembly 40. The conveyor system 50 further includes a trolley 58 for moving anode assemblies 40 via the bells 53. The conveyor system 50 may include a rod guiding mechanism (not illustrated) to position the anode assemblies 40 in a consistent orientation relative to the imaging system 20 during movement (e.g., coincidental to a plane that is perpendicular to the view of the imaging device 22).

The conveyor 50 may be configured, relative to the imaging system 20 and/or the light production system 60, such that images and/or measurements are made while the anode assemblies 40 are moving at normal speeds within the smelting facility. In one embodiment, the anode assemblies 40 are not required to stop or slow down, relative to normal operating speeds, during the image collection and/or physical measurement processes. Thus, normal smelting production throughput may be maintained, and normal anode production and/or metal production rates may be realized.

The conveyor system 50 may include other optional features for facilitating data collection and/or smelting management. For example, the conveyor system 50 may include a physical measurement device 52 and corresponding physical data collector, such as a weight measurement device for facilitating measurement of weights of the anode assemblies 40 and collecting weight data relating to the anode assemblies 40. The obtained physical data may be communicated to one or more computerized devices, such as the computer 24 of the imaging system 20, via wireless or wired technology. The conveyor system 50 may further include a data matrix (e.g., barcodes), RFIDs, transponders, and the like, to facilitate unique identification of each anode assembly. In one embodiment, the data matrix is compliant with ISO/IEC16022, also known as the International Symbology Specification, Data Matrix. In this regard, each of the trolleys 58 and/or anode rods 44 may include a unique data matrix, RFID 54 or transponder. Further, the anode analysis system 10 may include a scanner/reader 56 placed in a location suited to scan, read and/or receive signals from the data matrix, RFID, and/or transponder, and identify the unique identifier associated therewith. As used herein, "unique identifier" means a unique piece of information relative to other pieces of information of an information set. As the images are obtained, the unique identifier information may be communicated to the computer 24 of the imaging system 20, and/or to the control center 500. Thus, the obtained images, and therefore anode characteristic data of each anode assembly, may be correlated with a unique identifier.

As noted above, the imaging system 20 may be operable to obtain images of anode assemblies 40. After the images are obtained, they may be processed and/or analyzed. In one approach, the images are analyzed to determine geometrical characteristics of the anode assemblies. The obtained images may be analyzed via, for example, commercial image analysis software, such as LABVIEW from National Instrument. In one approach, an image analysis is performed, and geometrical measurements of the anode butts are determined. In one approach, a surface area or volume of an anode butt is determined, as described in further detail below. In one approach, the surface area or volume of a zone of an anode butt is determined, as described in further detail below. In one approach, angles related to the anode assemblies are determined, such as an angle associated with a bottom and/or top surface of the anode butt 42 relative to a horizontal line, or an angle of the rod 44 relative to a vertical line.

Figure 3:
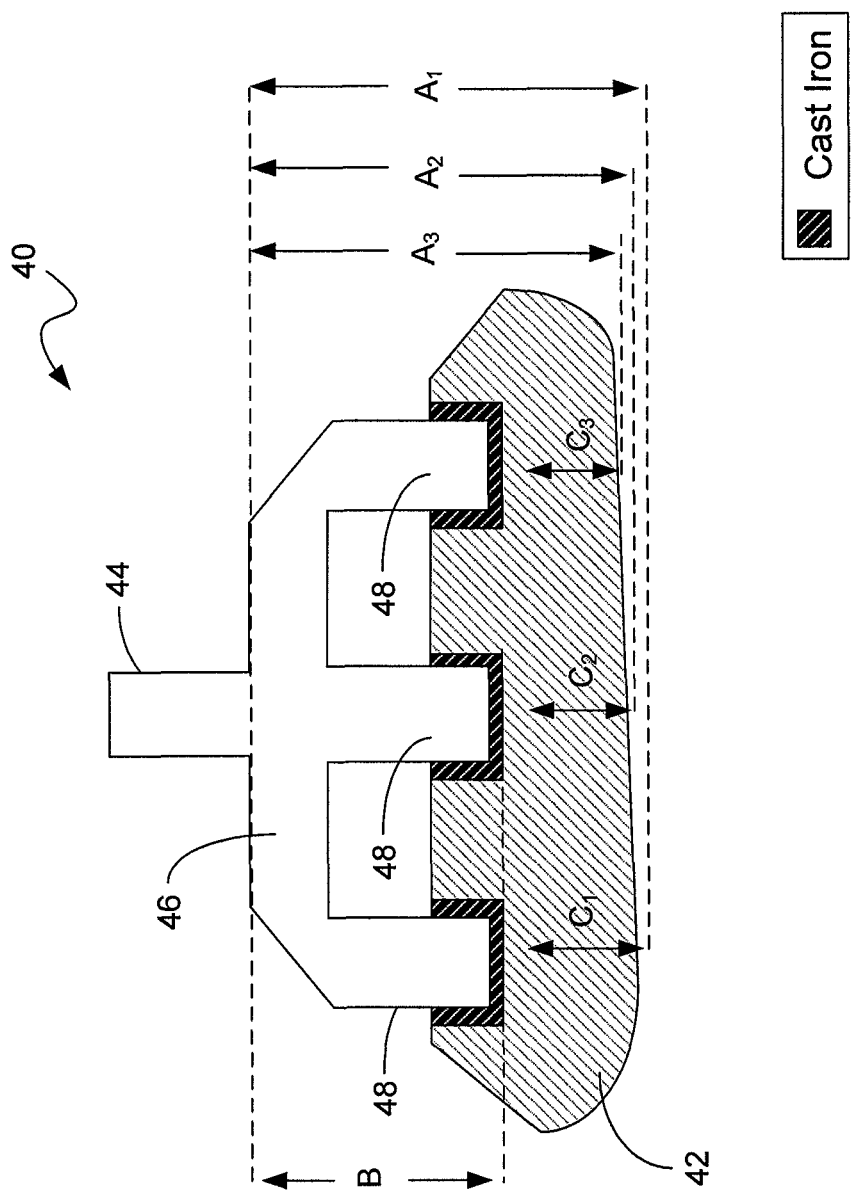
FIG. 3 illustrates one embodiment of an anode analysis methodology.

In one aspect, anode thickness information is determined. In one approach, the distance between a reference and surfaces of the anode butt may be determined. In one embodiment, and with reference to FIG. 3, the reference is the top of a horizontal traverse 46 of the anode rod 44, and the distance between the top of the horizontal traverse 46 and bottom portions of the anode that are coincidental to stubs 48 of the anode rod 44 are determined, as illustrated by A1, A2, and A3. In a related approach, distances between a reference and surfaces of the anode rod 44 may be determined. In one embodiment, the reference is the top of the horizontal traverse 46, and the distance between the top of the horizontal traverse 46 and an anode rod stub 48 may be determined, as illustrated by B. Using the instant approach, the distance between one or more anode rod stubs 48 and bottom portions of the anode butt 42 may be determined, as illustrated by C1, C2 and C3, which may facilitate calculation of, for example, anode butt thickness, described in further detail below. In the instant approach, a first image of the anode assembly may be obtained post-use (e.g., to facilitate calculation of A1-A3), and a second image of the anode assembly may be obtained post-recovery (e.g., to facilitate calculation of B). Other approaches are possible.

In one embodiment, anode butt thickness information is produced. Anode butt thickness information may facilitate management of smelting activities. For example, anode butt thickness(es) may be measured post-use to determine whether anodes are being efficiently utilized. If the anode butt thickness is too thick, the anode may have been prematurely removed from the electrolysis cell. If the anode butt thickness is too thin, the anode may have been tardily removed from the electrolysis cell. In either event, the anode butt thickness information may be used, by way of illustration, to adjust anode production operations (e.g., a coke-to-pitch ratio) and/ or electrolysis cell operations (e.g., an amount of time an anode assembly is used in an electrolysis cell), to name two.

Figure 4:
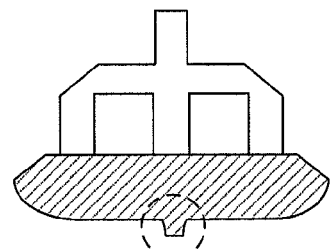
FIG. 4 illustrates various views of various types of anode butts.
Figure 4:
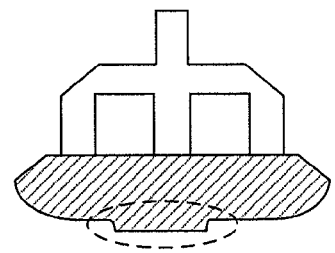
Figure 4:
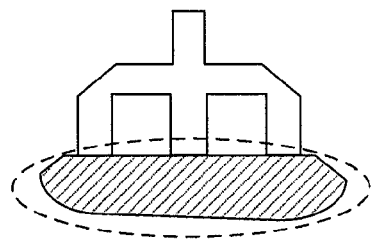
Figure 4:
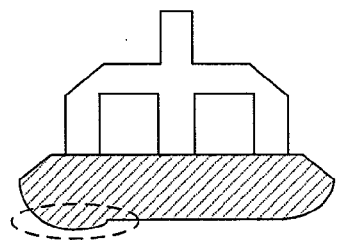
Figure 4:
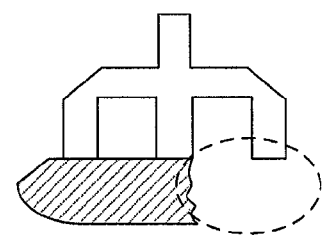
Figure 4:
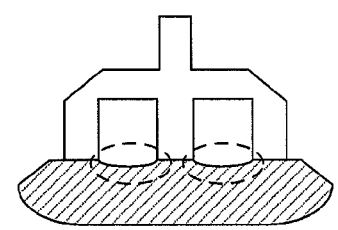

In one embodiment, defect information is produced. Determination of the geometrical characteristics of the anodes may facilitate determining whether the anodes contain defects. In turn, identification of these defects may be used to facilitate management of smelting activities. For example, and with reference to FIG. 4, a system may be operable to identify one or more families of defects from the obtained images. In the illustrated embodiment, the families of defects include:

Mushroom/Spike—Family 1
Belly—Family 2
Uneven—Family 3
Heel—Family 4
Incomplete—Family 5
Oxidized—Family 6

Mushroom defects, also known as spike defects, indicate the presence of coal dust in the electrolysis cell. Belly defects indicate that solids (e.g., a piece of an anode butt or solid bath) are present in the bottom of the electrolysis cell. These solids may be present due to pieces of an anode assembly breaking during anode replacement. Uneven defects indicate improper current distribution within the electrolysis cell, for example, due to the presence of plaque or mud on the cathode. Heel defects indicate improper current distribution within the electrolysis cell, for example, due to the crust and/or ledge accumulation in the pot. Incomplete defects indicate that the electrolyte crust was improperly broken during anode replacement and/or that the anode was excessively handled and/or that the anode was subjected to excessive oxidation. Oxidized defects indicate that the anode was excessively oxidized, for example, due to lack of anode cover material (alumina plus electrolyte bath particulate). Identification of these, and other, defects may facilitate management of smelting activities, as described in further detail below. Other defects are possible.

Figure 5:
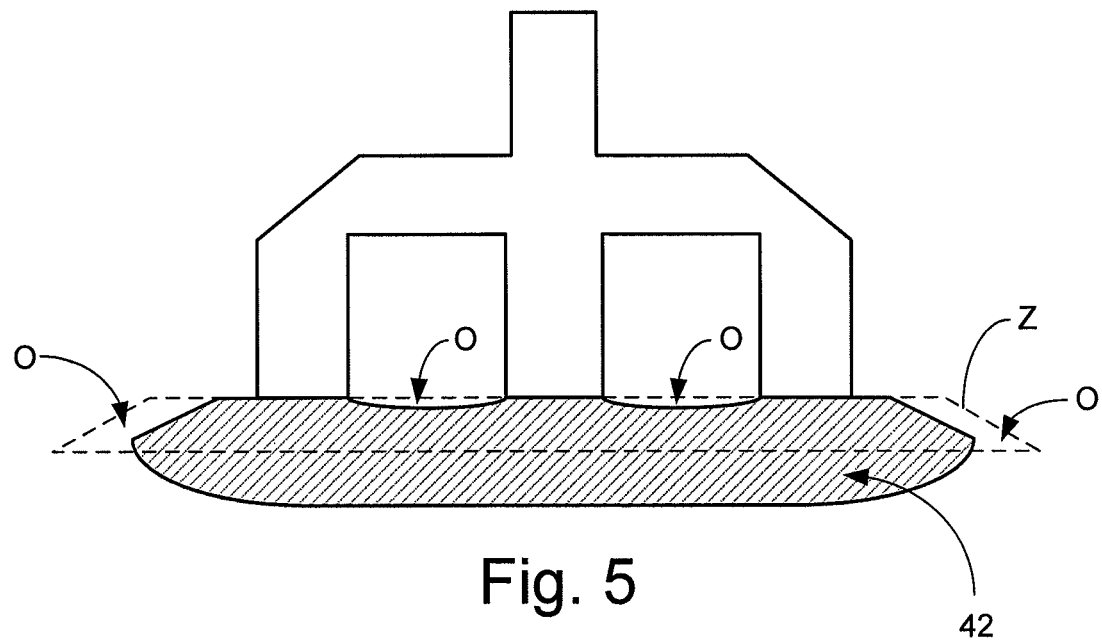
FIG. 5 is a schematic side view of an anode image having a zone coordinated therewith.

The defects may be determined using a variety of techniques. In one approach, the obtained images are compared to a standard image (e.g., an unused anode). "Oxidized" defects may be determined by comparing the obtained image relative to the standard image to determine the amount of oxidation of the anode. For example, and with reference to FIG. 5, the anode butt image may be coordinated with a standard image, or a portion thereof, as indicate by Z. The amount of oxidation may be determined by comparing the area of the anode butt image to the area of the standard image, as illustrated by O. A threshold oxidation value may be set based on historical data. Anodes that exceed this threshold oxidation value, e.g., as determined via the imaging system 20 and/or control center 500, may be automatically be categorized as anodes having oxidized defects.

Figure 6:
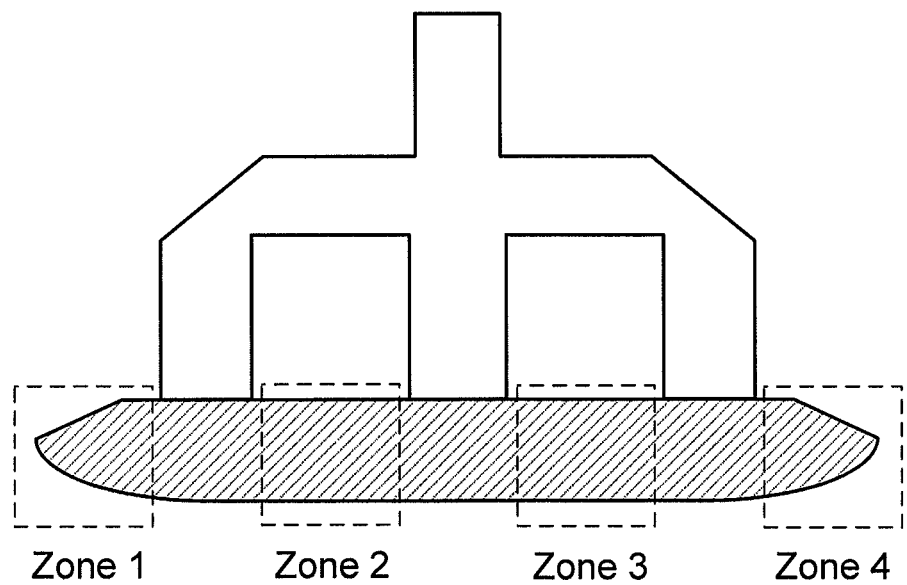
FIG. 6 is a schematic view of an anode image having multiple zones coordinated therewith.

"Incomplete" defects may be determined by determining whether an anode portion is located proximal each anode rod stub. To complete this analysis, one or more zones may be calculated and the area of these zones may be compared to threshold zone values to determine whether the anode butt includes an incomplete portion. For example, and with reference to FIG. 6, an amount of anode material in each of zones 1 through 4 may be determined. The determined amount of anode material in each of these zones may be compared to a threshold zone value (e.g., zone 1 threshold, zone 2 threshold, etc.) for each of these zones. If any one of the zone values is less than its corresponding threshold zone value, the anode may be automatically categorized as an anode having an incomplete defect.

Figure 7A:
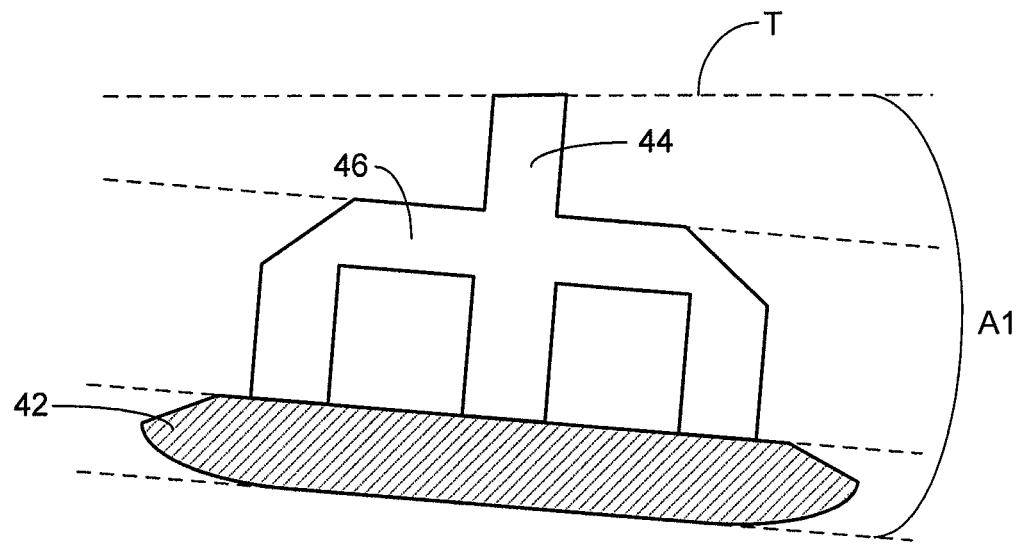
FIGS. 7a and 7b are schematic views of anode images having angles coordinated therewith.
Figure 7B:
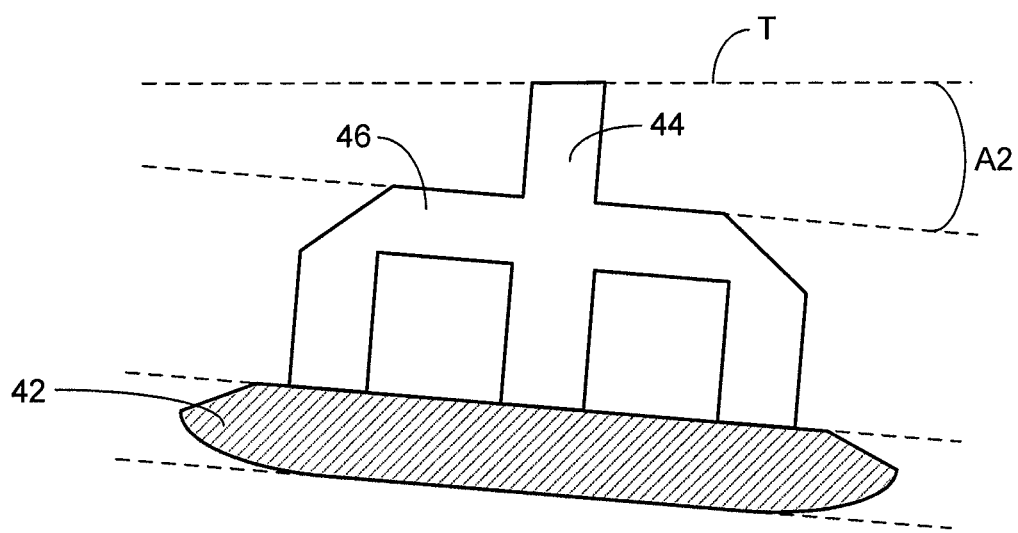

"Uneven" defects may be determined by comparing relative angles of various portions of the image and/or anode. In one approach, and with reference to FIGS. 7a-7b, an angle between surfaces of the anode butt 42 and the anode rod 44, or the top of the image may be compared. In the illustrated approach, a line associated with the horizontal traverse 46 is compared to the top (T) of the image to determine a reference angle A2 (FIG. 7b). A line associated with the bottom of the anode butt 42 is compared to the top of the image T to determine an anode angle A1 (FIG. 7a). The reference angle A1 may be compared to the reference angle A2 to determine a differential. If the differential exceeds a threshold value, the anode may be automatically categorized as an anode having an uneven defect.

"Mushroom", "belly" and "heel" defects may be determined by analyzing the butt of the anode assembly and determining a normal wear line based on the analysis. The wear of the anode butt, such as relative to the wear line, may then be analyzed to determine the geometrical characteristics of the anode butt. If the determined characteristics are not in accordance with a threshold, the characteristics may be categorized as anode anomalies and may be used to place the anode butts into one of the mushroom, belly and heel defects family. For example, anomalies having low width-to-height ratios (L/H) may be categorized as mushroom defects. Position information may also be used. For example, one or more anode zones may be determined, as described above. If the anomalies are positioned in zones coincidental to either of the outermost anode stubs, or any zone therebetween, the anomaly may be categorized as a belly. Anomalies outside of these zones may be categorized as a heel. Any combinations of the above techniques may be utilized to determine and categorize anomalies or defects. Moreover, other analysis techniques may be used to identify defects.

In another approach, the percent of bath remaining on the surface of the anode butt is determined. In this approach, a first image of an anode assembly is obtained via the imaging system. This first image may be obtained using a front light (e.g., a flash), such as light 36. A second image of the anode assembly may then be obtained. The second image may be obtained using a back light, such a lighting unit 60. Light differences (e.g., contrast) between the first and second images may be determined to determine anode characteristics, such as whether bath remains on the anode surface. In general, bath surfaces may appear white in the compared images, whereas anode portions may appears grayish or black.

Figure 8:
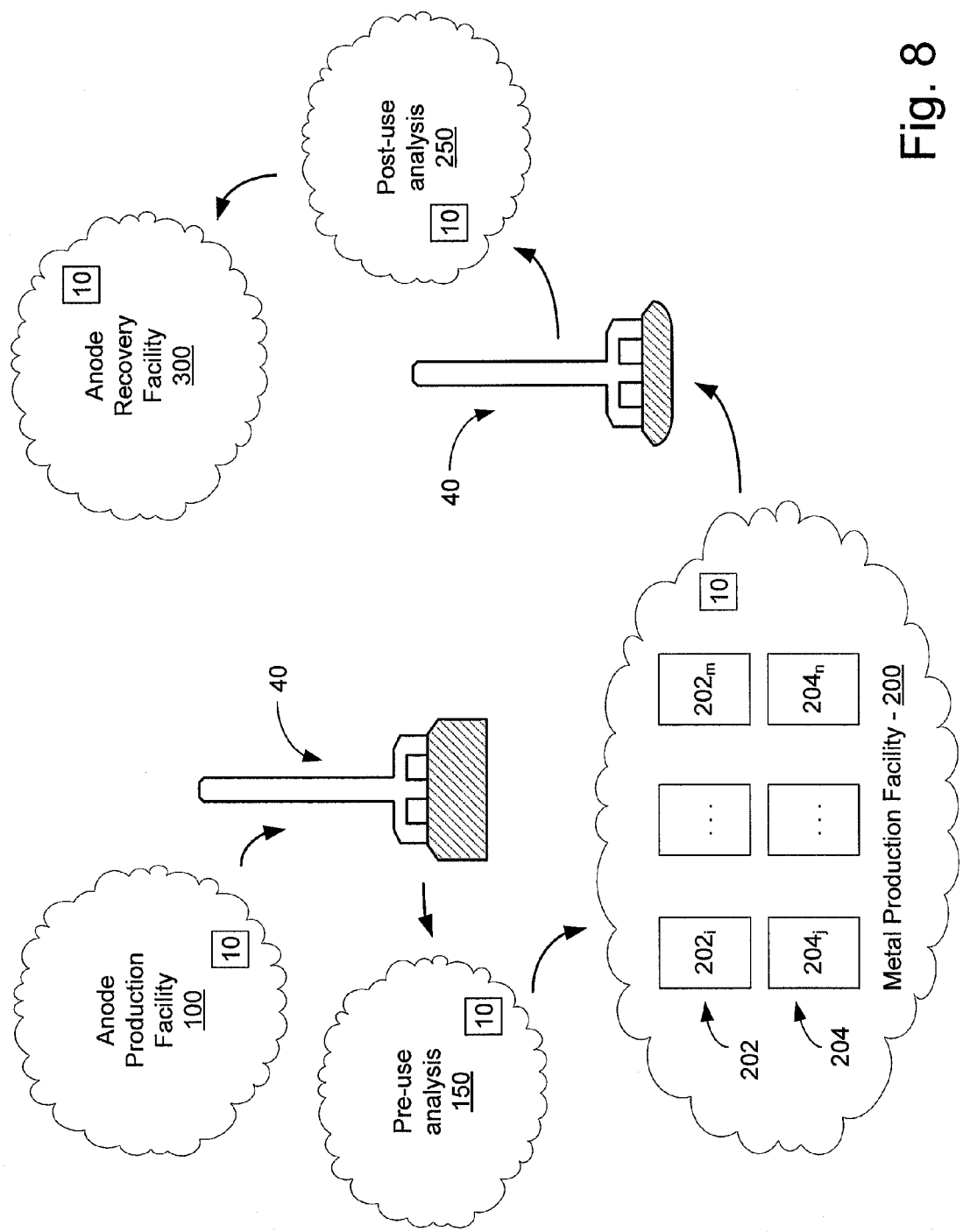
FIG. 8 is a schematic view illustrating one embodiment of a smelting production plant including various anode analysis systems.

As noted above, the anode analysis system 10 may be used to facilitate smelting activities. In this regard, the anode analysis system may be located at one or more locations of a smelting plant. For example, and with reference to FIG. 8, a smelting plant may include an anode production facility 100, a metal production facility 200, and an anode recovery facility 300. The anode production facility produces anode assemblies 40 for use in electrolysis cells of the metal production facility 200. The metal production facility may include a plurality of pot lines 202, 204, where each line includes a plurality of electrolysis cells $202_i$-$202_{i+j}$ and $204_m$-$204_{m+n}$, respectively. After use in the metal production facility 200, the anode rods and carbon of the anode assemblies 40 may be recovered in the anode recovery facility 300. A conveyor system (not illustrated) may be used to move anode assemblies 40 through the smelting plant, such as from the anode production facility 100 to the metal production facility 200, or from the metal production facility 200 to the anode recovery facility 300. One or more anode analysis systems 10 may be located in any one of these facilities 100, 200, 300 so as to facilitate obtaining images of pre-use, post-use and/or post-recovery anode assemblies. Images of the anode assemblies

40 may be obtained at any of these locations. In another embodiment, one or more anode analysis systems 10 may be located between the anode production facility 100 and the metal production facility 200, such as at location 150. In a related embodiment, one or more anode analysis systems 10 may be located between the metal production facility 200 and the anode recovery facility 300, such as at location 250. In one embodiment, images of anode assemblies 40 are obtained prior to removal of the anode butts 42 from the rod 44 to obtain images of the anode butts 42. In a related embodiment, images of anode assemblies 40 are obtained after removal of the anode butts 42 to obtain images of the rod 44 and one or more stubs 48. As described above, the anode analysis systems 10 may be integrated with conveyor systems to facilitate obtaining of images and anode characteristic data without disrupting the normal process flow of the smelting plant.

Figure 9:
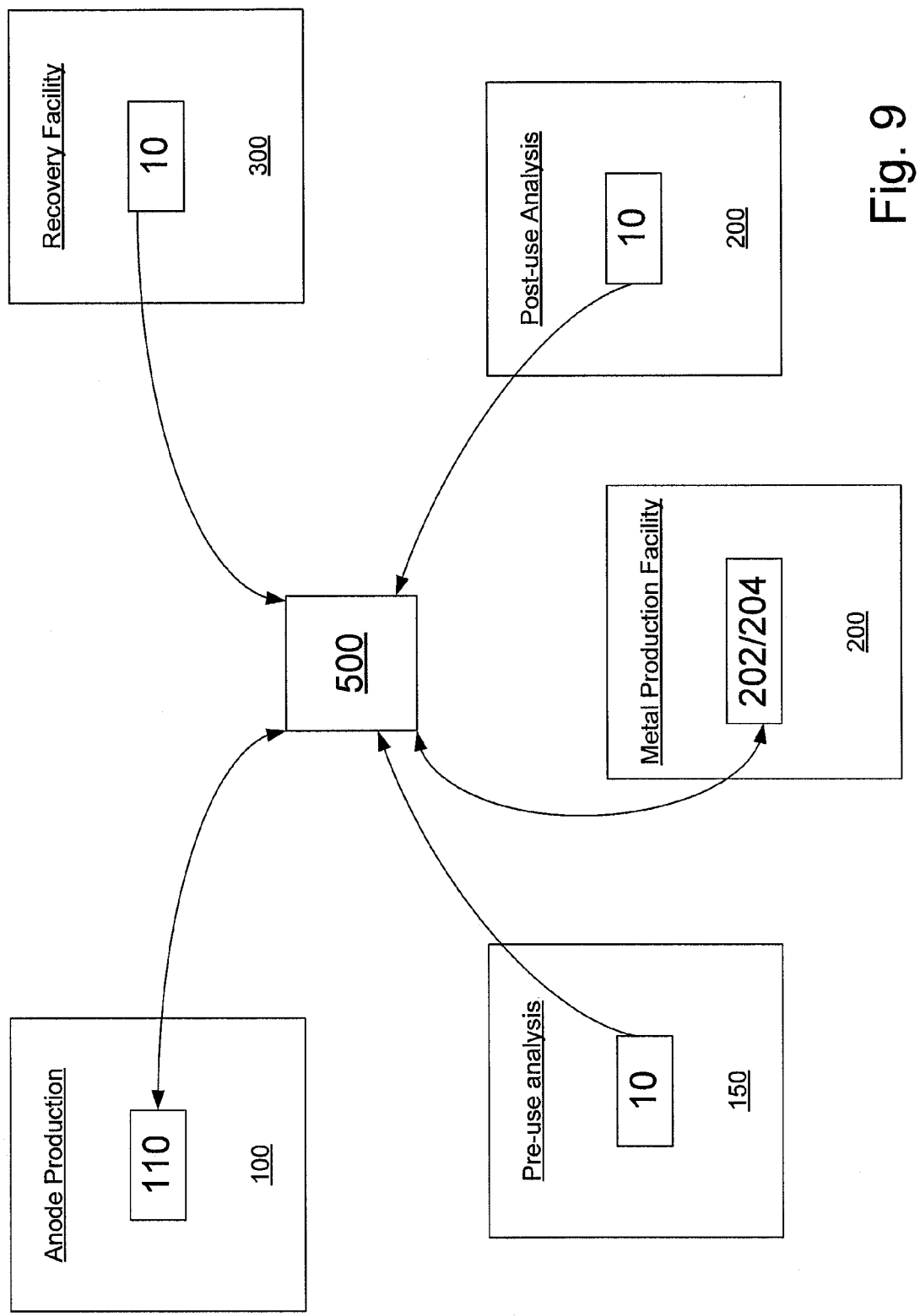
FIG. 9 is a schematic view illustrating one embodiment of data flow in a smelting production plant.

Anode characteristic data obtained via the anode analysis system 10 may be utilized to facilitate management of smelting activities. In one embodiment, and with reference to FIG. 9, anode analysis systems 10 may be located at location 150 between the anode production facility 100 and the metal production facility 200 to obtain images of pre-use anode assemblies and produce anode characteristic data based thereon. As anode assemblies 40 are conveyed from the anode production facility 100 to the metal production facility 200, images of the anode assemblies 40 may be obtained via the anode analysis system 10. The obtained images, imaging data and/or anode characteristic data may be communicated, via wired or wireless technology, to a control center 500. To facilitate identification of anode assemblies 40 and their associated anode characteristic data, data matrices, RFIDs, transponders, or other suitable means, may be employed with the anode assemblies 40 and/or conveyors 50, as described above, and each anode assembly 40 may be correlated with a unique identifier based thereon. Thus, the pre-use images, imaging data, and/or pre-use data may be correlated with its respective anode assembly 40 via the unique identifier.

Once the anode assemblies 40 are ready for use in a pot line of the metal production facility 200, various metal production data may be communicated to the control center 500, such as the pot line 202 or 204 in which the anode assembly 40 is to be used, the electrolysis cell in which the anode assembly 40 is to be used, and/or the location of the anode assembly 40 within the electrolysis cell (e.g., position 8 of 10 in the electrolysis cell, where 1 and 10 are end positions). This metal production data may be correlated with the unique identifier for each anode assembly 40 for use in smelting production analysis and management.

After use in the metal production facility 200, the anode assemblies 40 may be conveyed from the metal production facility 200 to the recovery facility 300. An anode analysis system 10 may be located at location 250 between the metal production facility 200 and the anode recovery facility 300 to obtain images of the anode assemblies 40 post-use, and produce anode characteristic data based thereon. The obtained images, imaging data and/or anode characteristic data may be communicated, via wired or wireless technology, to the control center 500. To facilitate identification of anode assemblies 40, data matrices, RFIDs, transponders, and the like, may be employed with the anode assemblies 40 and/or conveyors 50, as described above. Thus, the obtained post-use images, imaging data and/or anode characteristic data may be correlated with the pre-use images, imaging data and/or anode characteristic data and/or the metal production data, such as via the unique identifier.

After recovery in the anode recovery facility, images of the anode assemblies 40 may be obtained post-recovery to obtain images of the rod 44 and one or more stubs 48, and anode characteristic data may be produced based thereon via anode analysis system 10. To facilitate identification of anode assemblies 40, data matrices, RFIDs, transponders, and the like, may be employed with the anode assemblies 40 and/or conveyors 50, as described above. The obtained images, imaging data, and/or anode characteristic data may be communicated, via wired or wireless technology, to a control center 500. Thus, the obtained post-recovery images, imaging data, and/or anode characteristic data may be correlated with the post-use images, imaging data, and/or anode characteristic data, pre-use images, imaging data and/or anode characteristic data and/or the metal production data, such as via the unique identifier.

The control center 500 may be located remote of the facilities 100, 200, 300, or may be located within one of the facilities 100, 200, 300. As used herein, "remote" means not within the immediate vicinity. The control center may include any controller, such as a computerized device, to facilitate receipt of images, imaging data, anode characteristic data and/or smelting management. The control center may utilize the obtained images, imaging data, and/or anode characteristic data to facilitate management of smelting activities. For example, anode thicknesses may be determined. If an anode thickness is outside of a predetermined threshold, an anode production parameter may be adjusted (e.g., a coke-to-pitch ratio) such as by communication with a controller/computer display 110 of the anode production facility, or an electrolysis cell operating condition may be adjusted, such as via communication with pot lines 202/204. In another embodiment, the presence of anode defects (e.g., mushroom, heel, uneven, belly, incomplete oxidized) may be detected. In one embodiment, if anode defects are determined to be present, an appropriate action may be completed in response to the determination. In one embodiment, a mushroom defect is detected and an electrolysis cell associated with the defective anode is checked for presence of coal dust and/or is subjected to maintenance (e.g., cleaning of the electrolysis cell). In one embodiment, a belly defect is detected and an operator or manager associated with the electrolysis cell is notified of the belly defect. In one embodiment, an uneven defect is detected and electrolysis cell operating conditions are adjusted and/or the cathode is subjected to maintenance. In one embodiment, a heel defect is detected and alumina feed rates are checked/adjusted and/or the ledge/crust of the electrolysis cell is checked/manually broken. In one embodiment, an incomplete defect is detected and an operator or manager associated with the electrolysis cell is notified of the incomplete defect. In one embodiment an oxidized defect is detected, and additional cover material is provided to the cell, and/or an operator or manager associated with the electrolysis cell is notified of the oxidized defect. In some embodiments, operators may undergo further training to facilitate reduction of defective anodes.

Figure 10:
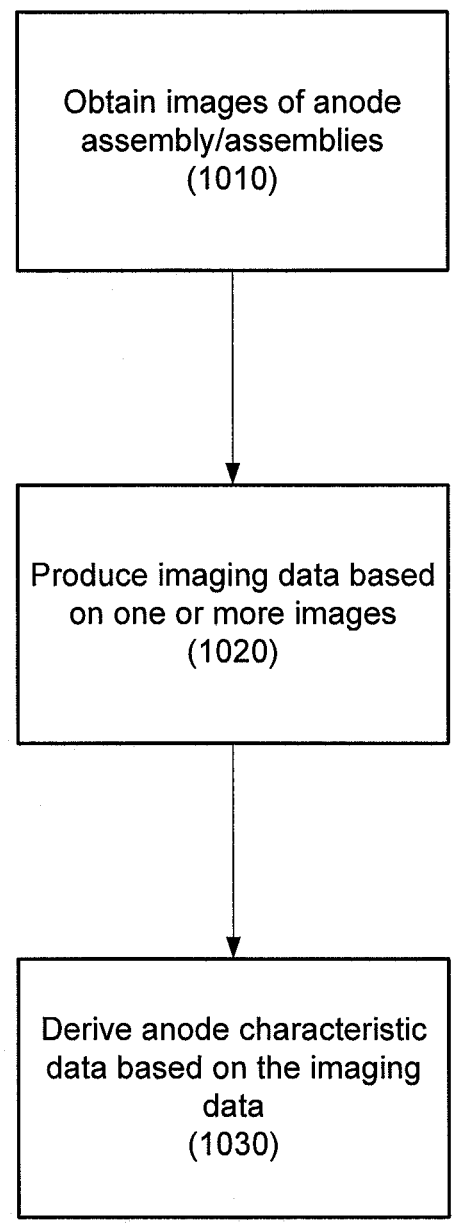
FIG. 10 is a flow chart illustrating one embodiment of a method relating anode inspection.

Methods relating to anode inspection and analysis are also provided. In one embodiment, and with reference to FIG. 10, a method may include the steps of obtaining at least one image of at least a portion of an anode assembly (1010), producing imaging data based on the at least one image (1020), and deriving anode characteristic data based, at least in part, on the imaging data (1030). In turn, the geometrical characteristics of the anode assembly may be determined. In one approach, an anode thickness, or a zone thereof, is determined. In one embodiment, it may determined whether the anode assembly includes a defect.

The method may include the step of utilizing the anode characteristic data to manage smelting activities in an aluminum smelting plant/facility. In one embodiment, a method includes the steps of utilizing the anode assembly in an aluminum electrolysis cell, and removing the anode assembly from the aluminum electrolysis cell. Anode characteristic data of the used anode assembly may be derived, as provided above. In turn, the anode characteristic data may be used to determine whether the aluminum electrolysis cell requires adjustment based on the anode characteristic data. In another approach, a method may include the step of producing the anode assembly in an anode production facility. Anode characteristic data of the unused anode assembly may be derived, as provided above. In turn, a method may include the step of determining whether anode production parameters require adjustment based on the anode characteristic data.

Figure 11A:
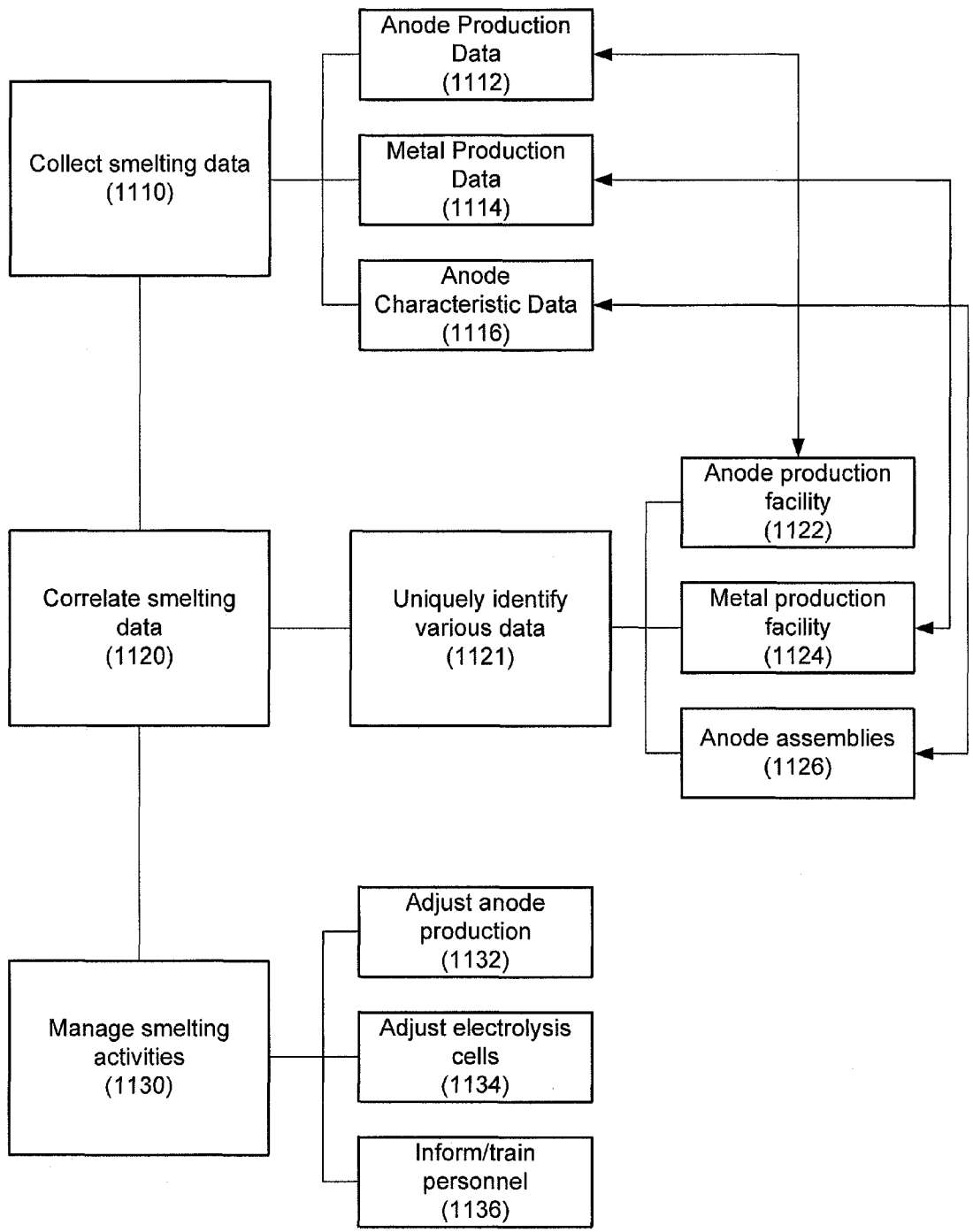
FIG. 11a is a flow chart illustrating one embodiment of a method relating to smelting management.

Methods of managing smelting activities are also provided. In one embodiment, and with reference to FIG. 11a, a method may include the steps of collecting smelting data (1110), correlating at least some of the smelting data (1120), and managing smelting activities (1130), such as based on the collected smelting data (1110), and/or correlating smelting data (1120) steps.

Figure 11B:
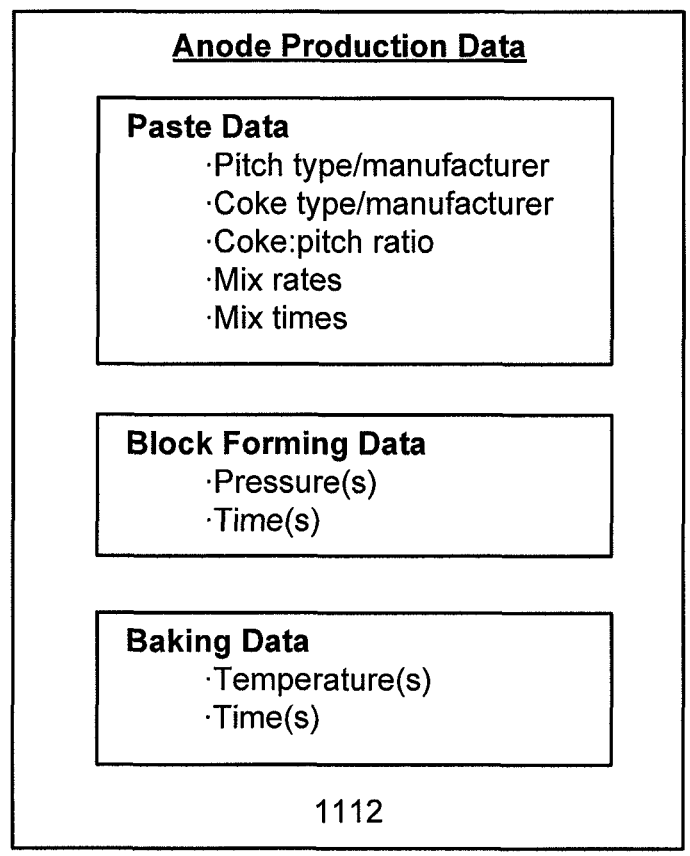
FIG. 11b is a chart illustrating various types of anode production data.

As described above, the collecting smelting data step (1110) may include collecting anode production data (1112), metal production data (1114), and/or anode characteristic data (1116). The anode production data (1112) may be collected from an anode production facility (1122). Anode production data may include, and with reference to FIG. 11b, paste data, block forming data and/or baking data, to name a few, and subsets of data associated therewith. Likewise, the metal production data (1114) may be collected from a metal production facility (1124). The metal production data may include, and with reference to FIG. 11c, potline data and/or electrolysis cell data, to name a few, and subsets of data associated therewith. The anode characteristic data (1116) may be collected via imaging of the anode assemblies (1126), and/or via physical data collection relating to the anode assemblies (1126), as described above. In this regard, the anode characteristic data may include, and with reference to FIG. 11d, geometrical features, such as thicknesses and/or defects associated with one or more of the anode assemblies. Lighting characteristics may also be included in the anode characteristic data, to determine, for example, an amount of bath remaining on the anode. In turn, the bath amount may be subtracted from the total calculated area to determine an area and/or volume of the anode assembly, or a portion thereof (e.g., the anode butt). The data may be collected pre-use, post-use, and/or post-recovery, as described above. To uniquely identify any of these data (1121), unique identifiers, such as data matrices, RFIDs, and transponders, may be utilized with any objects or systems associated with the anode production facility (1122), metal production facility (1124), and/or anode assemblies (1126).

Figure 11E:
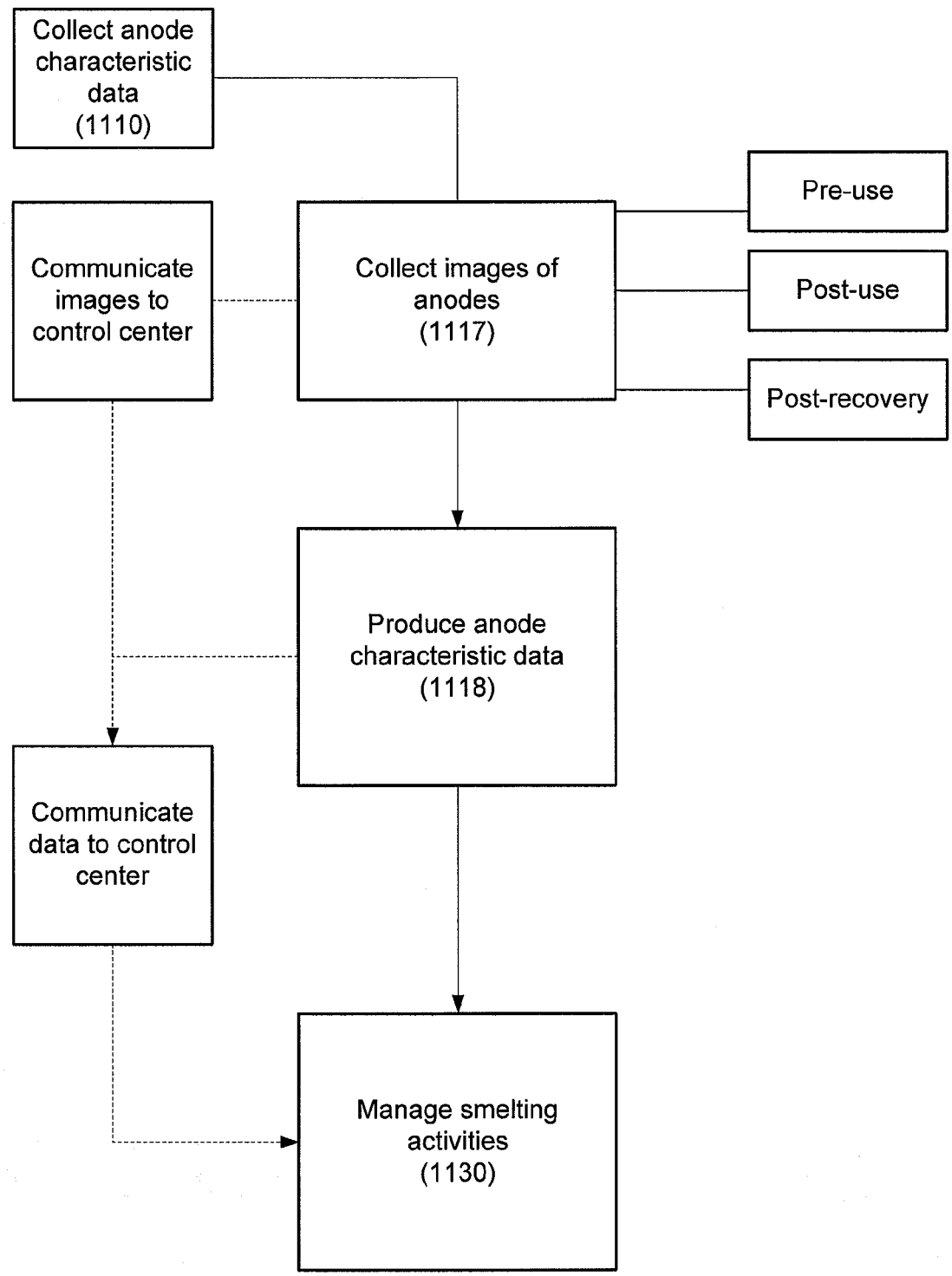
FIG. 11e is a flow chart illustrating one embodiment of a method for collecting anode characteristic data.

One embodiment of a method for collecting smelting data, and in this case anode characteristic data (1110), is illustrated in FIG. 11e. In the illustrated embodiment, the method includes the steps of collecting images of anodes (1117) and producing anode characteristic data based thereon (1118). The method may optionally include the step of managing smelting activities (1130) in response to the producing anode characteristic data step. With respect to the collecting images of anodes step (1117), the images may be collected pre-use, post-use and/or post-recovery, as described above. The images may then be analyzed (e.g., by an image analyzer described above), or communicated to a control center. With respect to the producing anode characteristic data step (1118), the anode characteristic data may be produced based on the collected images. In one embodiment, the anode characteristic data includes imaging data. In a related embodiment, the anode characteristic data also includes physical data. The anode characteristic data may be utilized to determine, for example, anode thicknesses and/or the presence of anode defects. The anode defects may be any of the mushroom, belly, uneven, heel, incomplete and/or oxidized defects described above. In one embodiment, the produced anode characteristic data is communicated to a control center. In other embodiments, the anode characteristic data is produced via an image processor and/or data analyzer at the control center, such as upon receipt of the anode images. With respect to the optional managing smelting activities step (1130), and referring now to FIGS. 11a and 11e, the anode characteristic data and information associated therewith may be utilized to adjust anode production (1132), adjust electrolysis cells (1134), and/or inform/train personnel of the smelting facility (1136), as described above. Other smelting activities may be managed with via the anode characteristic data.

Figure 11F:
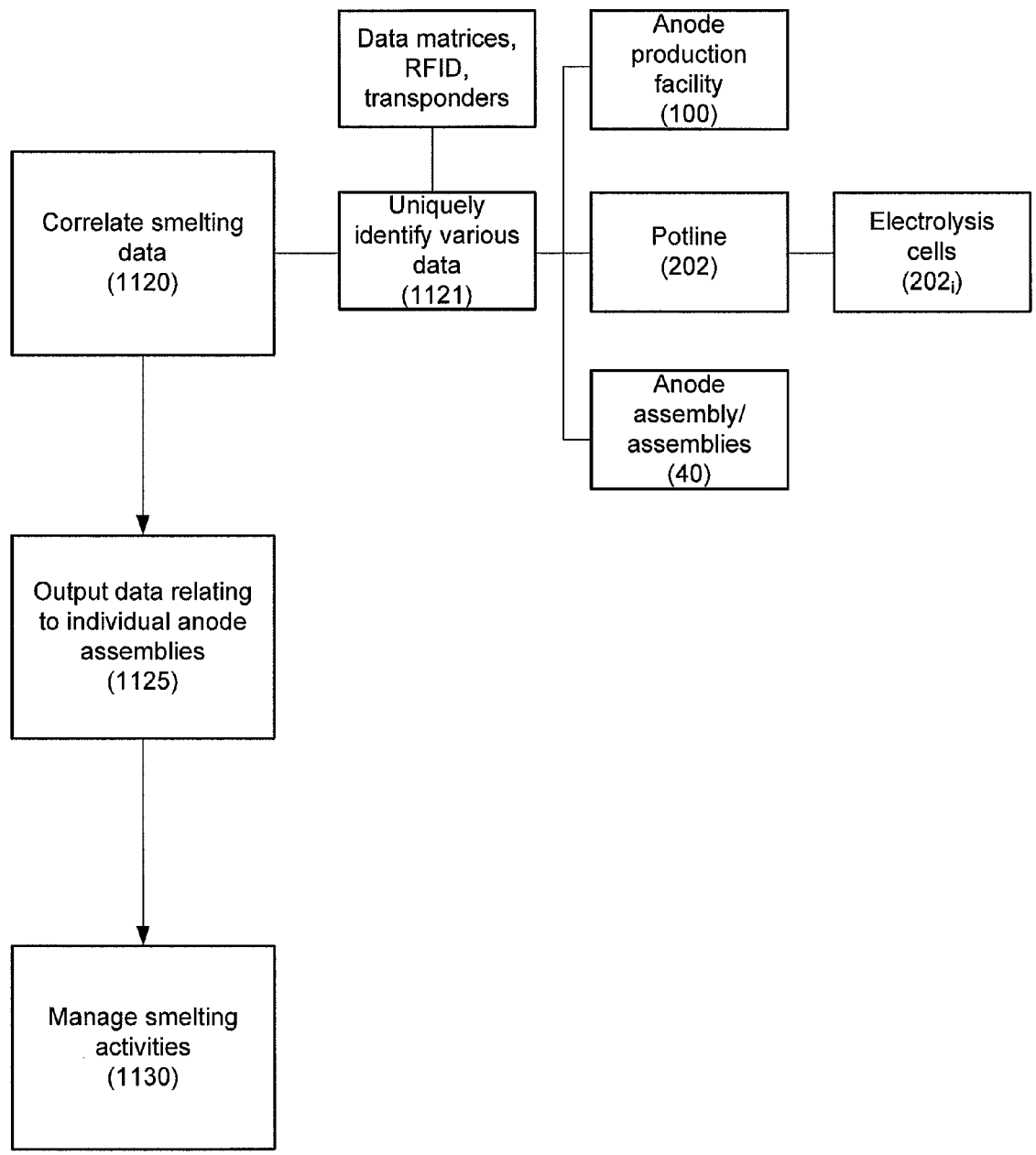
FIG. 11f is a flow chart illustrating one embodiment of a method for correlating smelting data.

Turning now to FIG. 11f, the correlating smelting data step (1120) may include the step of uniquely identifying various data (1121), such as data from any one of an anode production facility (100), a metal production facility (200), such as a potline (202) and/or an electrolysis cell (202$_i$), and/or an anode assembly (40). In one approach, data matrices, RFID, and/or transponders are utilized to uniquely identify various objects and/or materials utilized in any of the aforementioned areas and/or utilized with any of the aforementioned objects. For example, as described above, data matrices may be utilized with a conveyer and/or individual anode assemblies to facilitate unique identification of the anode assemblies. In turn, this unique identifier may be utilized to uniquely identify the produced imaging data and/or anode characteristic data that is produced for each of the anode assemblies. This uniquely identified data may be more readily utilized to facilitate managing smelting activities. In one embodiment, a unique identifier is correlated with at least one of the imaging data and the anode characteristic data via a computerized device. A scanner may be utilized to scan a member associated with the anode assembly, such as the trolley and/or bell of the conveyer, or a rod of the anode assembly. In turn, the unique identifier information may be communicated to a computerized device and correlated with the imaging data and/or anode characteristic data. The method may further include the step of outputting data relating to the individual anode assemblies (1125), so as to facilitate management of the smelting activity step (1130).

Figure 12:
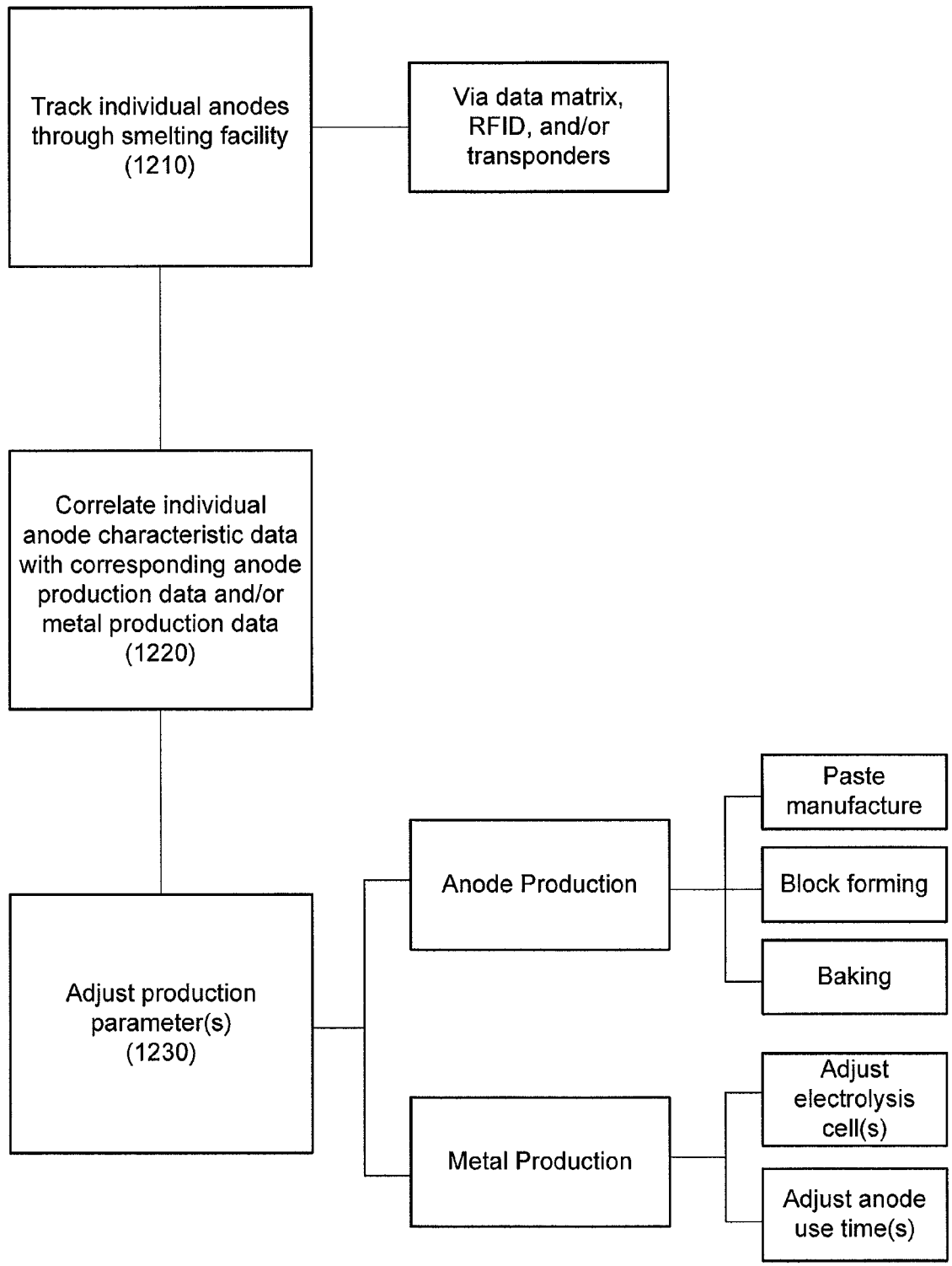
FIG. 12 is a flow chart illustrating one embodiment of a method for managing smelting activities.

In another approach, and with reference to FIG. 12, a method may include the steps of tracking individual anodes through a smelting facility (1210), correlating individual anode characteristic data with the corresponding anode production data and/or metal production data (1220), and adjusting production parameters based on at least some of the data (1230). As described above, the individual anodes may be tracked through the smelting facility via data matrices, RFIDs and/or transponders, to name a few. The correlated data may be utilized to adjust production parameters (1230). In one embodiment, anode production is adjusted, such as adjustment of paste manufacturer, block forming, and/or baking steps. In one embodiment, metal production is adjusted, such as adjustment of electrolysis cell operating conditions and/or adjustment of the amount of time anodes are used within an electrolysis cell.

Figure 13:
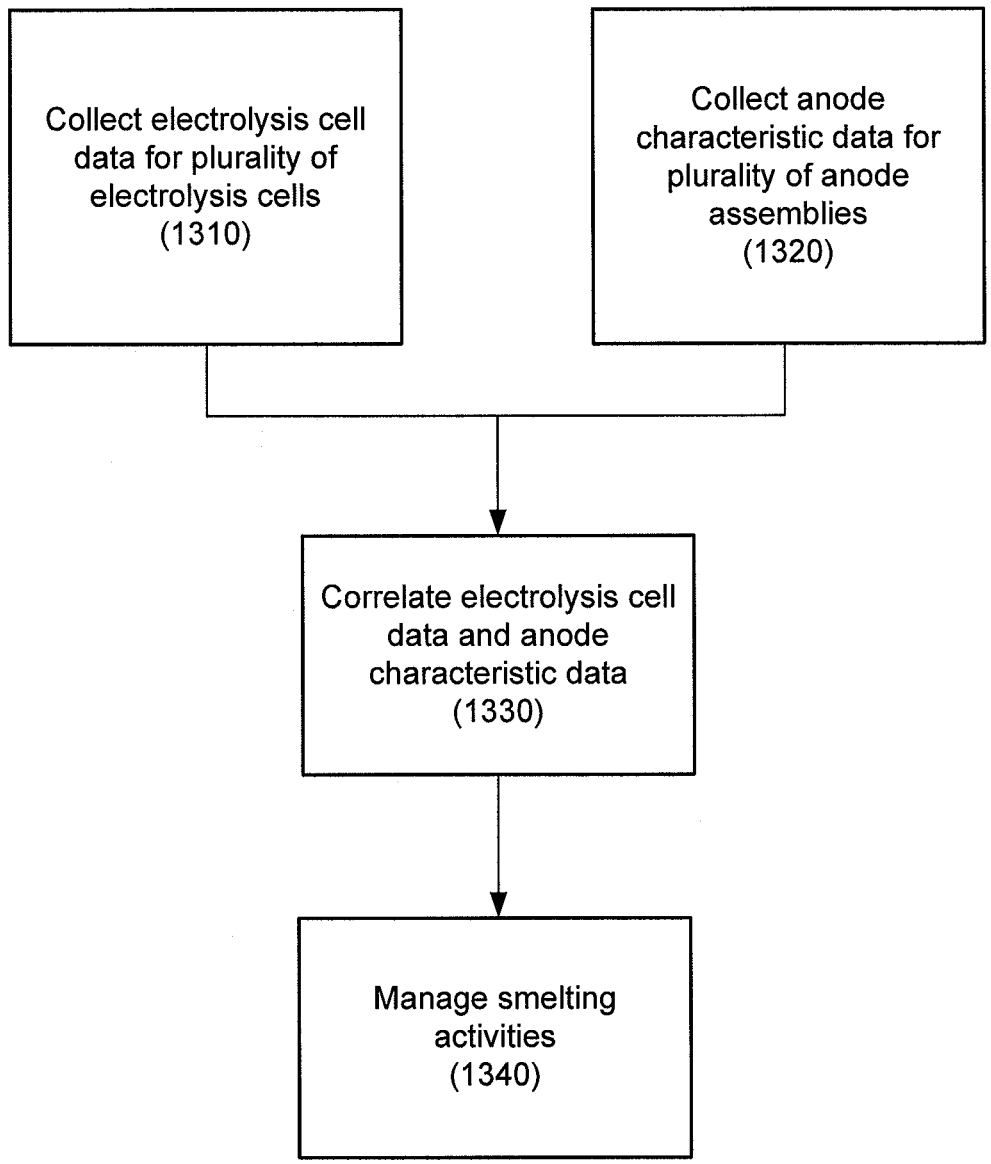
FIG. 13 is a flow chart illustrating one embodiment of a method for managing smelting activities.

In another approach, and with reference to FIG. 13, a method includes the steps of collecting electrolysis cell data for a plurality of electrolysis cells (1310), such as aluminum electrolysis cells, collecting anode characteristic data for a plurality of anode assemblies that are associated with the plurality of aluminum electrolysis cells (1320), correlating the electrolysis cell data and the anode characteristic data (1330), and managing smelting activities based on the data (1340). In one approach, the electrolysis cell data and anode characteristic data are correlated such that the anode characteristic data for each anode assembly corresponds with the electrolysis cell data for the electrolysis cell in which the anode assembly was used.

Various ones of the previously described systems, apparatus and/or steps of the above described embodiments may be combined or utilized with one another. More over various ones of the steps may be completed in parallel, while others may be completed in serial. Thus, various method steps may be completed concomitant to other method steps.

While the present disclosure has been described in terms of use of systems and methods for aluminum smelting, it will be appreciated that the described imaging systems may be utilized for smelting of other metals. Furthermore, while the instant disclosure has been described in reference to anodes, it will be appreciated that the instant disclosure may also be employed with respect to other types of electrodes, such as cathodes. Moreover, while various embodiments of the present disclosure have been described in detail, it is apparent that modifications and adaptations of those embodiments will occur to those skilled in the art. However, it is to be expressly understood that such modifications and adaptations are within the spirit and scope of the present invention.

What is claimed is:

1. A system comprising:
   (a) an imaging device configured to obtain at least one image of at least one used anode;
      wherein the used anode has been used in an electrolysis cell;
   (b) an image processor configured to produce imaging data based on the at least one image; and
   (c) a data analyzer configured to produce anode characteristic data based on the imaging data;
   wherein the data analyzer is configured to determine geometrical characteristics of the used anode based on the at least one image;
   wherein the data analyzer is configured to determine anode thicknesses for various zones of the used anode.

2. The system of claim 1, further comprising:
   a display adapted to display at least some of the anode characteristic data.

3. The system of claim 2, wherein the display is remote of the imaging system.

4. The system of claim 1, wherein the imaging device and image processor are integral.

5. The system of claim 1, wherein the image processor and data analyzer are integral.

6. The system of claim 1, wherein the data analyzer is configured to determine whether the used anode is defective.

7. A system comprising:
   (a) a mechanical conveyor system configured to convey at least one used anode assembly through an aluminum smelting facility;
      wherein the used anode assembly has been used in an electrolysis cell;
   (b) an imaging system located proximal the mechanical conveyor system and configured to obtain at least one image of the used anode assembly and produce anode characteristic data based thereon;
   (c) a computerized device configured to receive the anode characteristic data
   (d) a plurality of unique identifiers; and
   (e) a reader configured to read each unique identifier and communicate the unique identifier to at least one of the imaging system and the computerized device;
   wherein each unique identifier is associated with a used anode assembly, and wherein at least one of the imaging system and the computerized device is configured to correlate each unique identifier to a corresponding used anode assembly;
   wherein the anode characteristic data includes data relating to each unique identifier correlated to its corresponding, used anode assembly;
   wherein the computerized device is configured to assist in managing smelting facility activities based on the anode characteristic data; and
   wherein the plurality of unique identifiers is a first set of unique identifiers, and wherein the system further includes:
   electrolysis cell data obtained from a plurality of electrolysis cells; and
   a second set of unique identifiers, wherein each of the second set of unique identifiers is associated with one of the plurality of electrolysis cells, and wherein the electrolysis cell data includes data relating to each one of the second set of unique identifies correlated to its corresponding electrolysis cell.

8. The system of claim 7, wherein the computerized device is configured to assist in management of at least some of the plurality of electrolysis cells based, at least in part, on at least some of the electrolysis cell data and at least some of the anode characteristic data.

* * * * *